US011819330B2

(12) United States Patent
Kishi et al.

(10) Patent No.: US 11,819,330 B2
(45) Date of Patent: Nov. 21, 2023

(54) ATTENTION ABILITY INSPECTION DEVICE AND ATTENTION ABILITY INSPECTION METHOD

(71) Applicant: TOYOTA JIDOSHA KABUSHIKI KAISHA, Aichi-ken (JP)

(72) Inventors: Hiroshi Kishi, Toyota (JP); Kentaro Yokoi, Toyota (JP)

(73) Assignee: TOYOTA JIDOSHA KABUSHIKI KAISHA, Aichi-ken (JP)

( * ) Notice: Subject to any disclaimer, the term of this patent is extended or adjusted under 35 U.S.C. 154(b) by 218 days.

(21) Appl. No.: 17/471,090

(22) Filed: Sep. 9, 2021

(65) Prior Publication Data

US 2022/0079486 A1 Mar. 17, 2022

(30) Foreign Application Priority Data

Sep. 11, 2020 (JP) .................. 2020-152669

(51) Int. Cl.
*A61B 5/16* (2006.01)
*A61B 5/00* (2006.01)

(52) U.S. Cl.
CPC .............. *A61B 5/168* (2013.01); *A61B 5/162* (2013.01); *A61B 5/163* (2017.08); *A61B 5/742* (2013.01); *A61B 5/7475* (2013.01)

(58) Field of Classification Search
CPC ....... A61B 5/742; A61B 5/7475; A61B 5/162; A61B 5/168; A61B 5/163
See application file for complete search history.

(56) References Cited

U.S. PATENT DOCUMENTS

| | | | | |
|---|---|---|---|---|
| 4,028,819 A | * | 6/1977 | Walker .................. | A61B 5/165 434/258 |
| 4,971,434 A | * | 11/1990 | Ball ...................... | A61B 3/032 351/224 |
| 2011/0279676 A1 | * | 11/2011 | Terada .................. | G08B 21/02 348/148 |

(Continued)

FOREIGN PATENT DOCUMENTS

| | | |
|---|---|---|
| JP | 2010-254201 A | 11/2010 |
| JP | 2011-180873 A | 9/2011 |

(Continued)

OTHER PUBLICATIONS

Tomoki Ohashi et al., Visual attention on the central vision, Institute of Nuclear Safety System, Incorporated and Tohoku University, The Japanese Journal of Psychonomic Science, Published Sep. 30, 2000, pp. 33-34, vol. 19, No. 1, 2pp.

*Primary Examiner* — Daniel L Cerioni
(74) *Attorney, Agent, or Firm* — HAUPTMAN HAM, LLP

(57) ABSTRACT

In an attention ability inspection method, at least one of a central task of unsteadily changing a central graphic at a predetermined speed and a peripheral task of displaying a peripheral graphic in a peripheral region of a display area is randomly presented in a state in which the central graphic is displayed in a central region of the display area of a display, time from presentation of the central task or the peripheral task to reception of a predetermined operation from a subject that has recognized the presentation is measured as reaction time, and an attention ability of the subject is evaluated based on the reaction time.

20 Claims, 12 Drawing Sheets

(56) References Cited

U.S. PATENT DOCUMENTS

| | | | |
|---|---|---|---|
| 2012/0154751 A1* | 6/2012 | Pelah | G06V 40/19 |
| | | | 351/224 |
| 2012/0208170 A1 | 8/2012 | Kimura et al. | |
| 2015/0141865 A1* | 5/2015 | Nakajima | A61B 5/6803 |
| | | | 600/558 |
| 2015/0305663 A1* | 10/2015 | Roots | A61B 5/168 |
| | | | 600/595 |
| 2017/0240109 A1* | 8/2017 | Kimura | G08G 1/16 |
| 2018/0336796 A1* | 11/2018 | Delis | A61B 5/7435 |
| 2020/0060603 A1* | 2/2020 | Bower | A61B 5/0075 |
| 2020/0077937 A1* | 3/2020 | Richer | A61B 5/6814 |
| 2021/0188289 A1* | 6/2021 | Oba | G08G 1/00 |

FOREIGN PATENT DOCUMENTS

| | | |
|---|---|---|
| JP | 2012-165956 A | 9/2012 |
| WO | 2009075385 A1 | 6/2009 |

\* cited by examiner

VISUAL ATTENTION ABILITY IN CASE IN WHICH FIRST
NON-VISUAL TASK IS PROCESSED IN PARALLEL

VISUAL ATTENTION ABILITY IN CASE IN WHICH SECOND
NON-VISUAL TASK IS PROCESSED IN PARALLEL

ATTENTION ABILITY INSPECTION DEVICE AND ATTENTION ABILITY INSPECTION METHOD

CROSS REFERENCE TO RELATED APPLICATION

This application claims priority to Japanese Patent Application No. 2020-152669 filed on Sep. 11, 2020, which is incorporated herein by reference in its entirety including the specification, claims, drawings, and abstract.

TECHNICAL FIELD

The present description discloses an attention ability inspection device and an attention ability inspection method for inspecting a visual attention ability of a subject.

BACKGROUND

An information processing ability that a person can exhibit to process a target task (for example, a task of driving and operating a vehicle) varies depending on the visual attention ability of the person. In particular, in a case of driving an automobile, it is said that 90% of information to be processed is visual information, and the level of the visual attention ability is very important in processing a task of driving an automobile.

Such a visual attention ability varies greatly depending on the characteristics inherent in each person, the arousal level, the content of other tasks to be processed in parallel, and the like. Also, the visual attention ability in a space is not uniform but usually distributes continuously in a mountain shape so that the visual attention ability is the highest in the central vision and is rapidly lowered from the center toward the peripheral vision.

In recent years, there has been demand for an attention ability inspection device that accurately inspects a level of such a visual attention ability and distribution from the central vision to the peripheral vision. Such an inspection device is used for determining whether or not a subject has a visual attention ability suitable for processing of a target task (for example, a task of driving a vehicle). Also, in recent years, there are cases in which an inquiry is made by voice from the vehicle side to the driver while the driver is driving the vehicle. In a case in which the content of such an inquiry is complicated, the visual attention ability may be lowered. The attention ability inspection device can also be used to evaluate how the visual attention ability of the subject changes depending on the content of such an inquiry. However, conventionally, there has been no attention ability inspection device that can accurately measure the visual attention ability, particularly, the distribution of the visual attention ability in the visual field space.

Note that WO 2009/075385 A discloses a visual field inspection device that inspects a visual field of a subject by sequentially displaying three types of visual inspection targets at predetermined display positions at the periphery of a central visual fixation target displayed at a predetermined position on a display screen and examining whether or not the subject can visually recognize each of the visual inspection targets displayed at the periphery of the central visual fixation target while gazing at the central visual fixation target. However, WO 2009/075385 A merely measures a visual field range of the subject and does not inspect an attention ability. Also, in WO 2009/075385 A, even in a case in which the degree to which the subject gazes at the central visual fixation target changes, the degree cannot be detected. Therefore, in WO 2009/075385 A, the inspection can be continued even in a state in which the subject does not appropriately gaze at the central visual fixation target, and as a result, the visual field range and the attention ability at the periphery of the visual field cannot be measured accurately.

Therefore, the present description discloses an attention ability inspection device and an attention ability inspection method that can more accurately inspect distribution of a visual attention ability from a central vision to a peripheral vision.

SUMMARY

An attention ability inspection device disclosed in the present description includes a display that displays an image in a display area, an input device that receives an operation from a subject, and a controller that controls a display content in the display area and determines an attention ability of the subject based on an operation content of the input device performed by the subject in response to a displayed image. The controller randomly presents at least one of a central task of unsteadily changing a central graphic at a predetermined speed and a peripheral task of displaying a peripheral graphic in a peripheral region of the display area in parallel with steady display in which the central graphic is displayed in a central region of the display area; measures, as reaction time, time from presentation of the central task or the peripheral task to reception of a predetermined operation from the subject that has recognized the presentation; and evaluates the attention ability of the subject based on the reaction time.

By randomly presenting at least one of the central task and the peripheral task, both a visual attention ability at a center of a visual field and a visual attention ability at a periphery of the visual field can be evaluated. Accordingly, distribution of a visual attention ability from a central vision to a peripheral vision can be measured more accurately.

In this case, the controller may evaluate the attention ability at the center of the visual field based on the reaction time to the central task and evaluate the attention ability at the periphery of the visual field based on the reaction time to the peripheral task.

With such a configuration, the visual attention ability at the center of the visual field and the visual attention ability at the periphery of the visual field can be evaluated individually. Accordingly, distribution of a visual attention ability from a central vision to a peripheral vision can be measured more accurately.

Also, the controller may repeat an inspection set a plurality of times in one inspection flow; the inspection set that starts with presentation of either the central task or the peripheral task once and ends with reception of the predetermined operation or timeout may be regarded as one set, and the controller may evaluate the attention ability of the subject based on the reaction time obtained in each of the plurality of inspection sets.

By repeating the inspection set a plurality of times, the visual attention ability can be inspected more accurately.

Also, the number of times of presentation of the central task may be greater than the number of times of presentation of the peripheral task in the one inspection flow.

In many target tasks, such as a task of driving an automobile, the visual attention ability at the center of the visual field is more important than the visual attention ability at the periphery of the visual field. By increasing the number of times of execution of the central task, the visual attention ability at the center of the visual field, which is more important, can be measured more accurately. In addition, by increasing the number of times of presentation of the central task, the subject can naturally easily focus on the center of the visual field and can easily keep the line of sight of the subject to the central region. As a result, the attention ability can be inspected more accurately.

Also, the controller may randomly change a timing from start of the inspection set to presentation of the central task or the peripheral task.

With such a configuration, the attention ability can be inspected in a more natural state. As a result, the attention ability can be inspected more accurately.

Also, the controller may be capable of changing a ratio of the number of times of presentation of the central task to the peripheral task in the one inspection flow.

Depending on the purpose of the attention ability inspection, the attention ability at the center of the visual field and the attention ability at the periphery of the visual field have different importance levels. According to the above configuration, since the ratio of the number of times of presentation of the central task to the peripheral task can be changed depending on the purpose of the attention ability inspection, the attention ability inspection more suitable for the purpose can be performed.

Also, the controller may cause the central graphic to blink without relevance to presentation of the central task in the steady display.

With such a configuration, in order to determine whether or not the central graphic is changed, the subject needs to temporarily memorize in the brain memory the central graphic before extinction and compare the central graphic memorized in the brain memory with the central graphic displayed again. As a result, the state of the brain memory is reflected on the evaluation result of the attention ability, and an inspection more suitable for practical use can be performed.

Also, the controller may cause the central graphic to move along a predetermined moving route without relevance to presentation of the central task in the steady display.

With such a configuration, in order to determine whether or not the central graphic is changed, the subject needs to temporarily memorize in the brain memory the central graphic after movement and compare the predicted central graphic with the actual central graphic. As a result, the state of the brain memory is reflected on the evaluation result of the attention ability, and an inspection more suitable for practical use can be performed.

Also, the predetermined operation may include a first operation corresponding to the central task and a second operation corresponding to the peripheral task and different from the first operation.

By making the operation corresponding to the central task and the operation corresponding to the peripheral task different from each other, the reaction to the central task and the reaction to the peripheral task can be distinguished clearly and detected, and the evaluation accuracy of the attention ability can be further improved.

Also, the peripheral graphic may be a Landolt ring graphic, and the second operation may be an operation of indicating a direction in which the Landolt ring graphic is open.

With such a configuration, the subject needs to perform not only grasping whether or not the peripheral graphic is presented but also information processing of grasping the shape of the peripheral graphic. As a result, it is possible to determine whether or not the peripheral region functions for the subject as an effective visual field; that is, a region in which information processing can be performed simultaneously with viewing.

An attention ability inspection method disclosed in the present description includes randomly presenting at least one of a central task of unsteadily changing a central graphic at a predetermined speed and a peripheral task of displaying a peripheral graphic in a peripheral region of a display area in a state in which the central graphic is displayed in a central region of the display area of a display; measuring, as reaction time, time from presentation of the central task or the peripheral task to reception of a predetermined operation from a subject that has recognized the presentation; and evaluating an attention ability of the subject based on the reaction time.

By randomly presenting the central task and the peripheral task, both the visual attention ability at the center of the visual field and the visual attention ability at the periphery of the visual field can be evaluated. Accordingly, distribution of a visual attention ability from a central vision to a peripheral vision can be measured more accurately.

According to the technology disclosed in the present description, the distribution of the visual attention ability from the central vision to the peripheral vision can be measured more accurately.

BRIEF DESCRIPTION OF DRAWINGS

Embodiment(s) of the present disclosure will be described based on the following figures, wherein.

DESCRIPTION OF EMBODIMENTS

Figure 1:
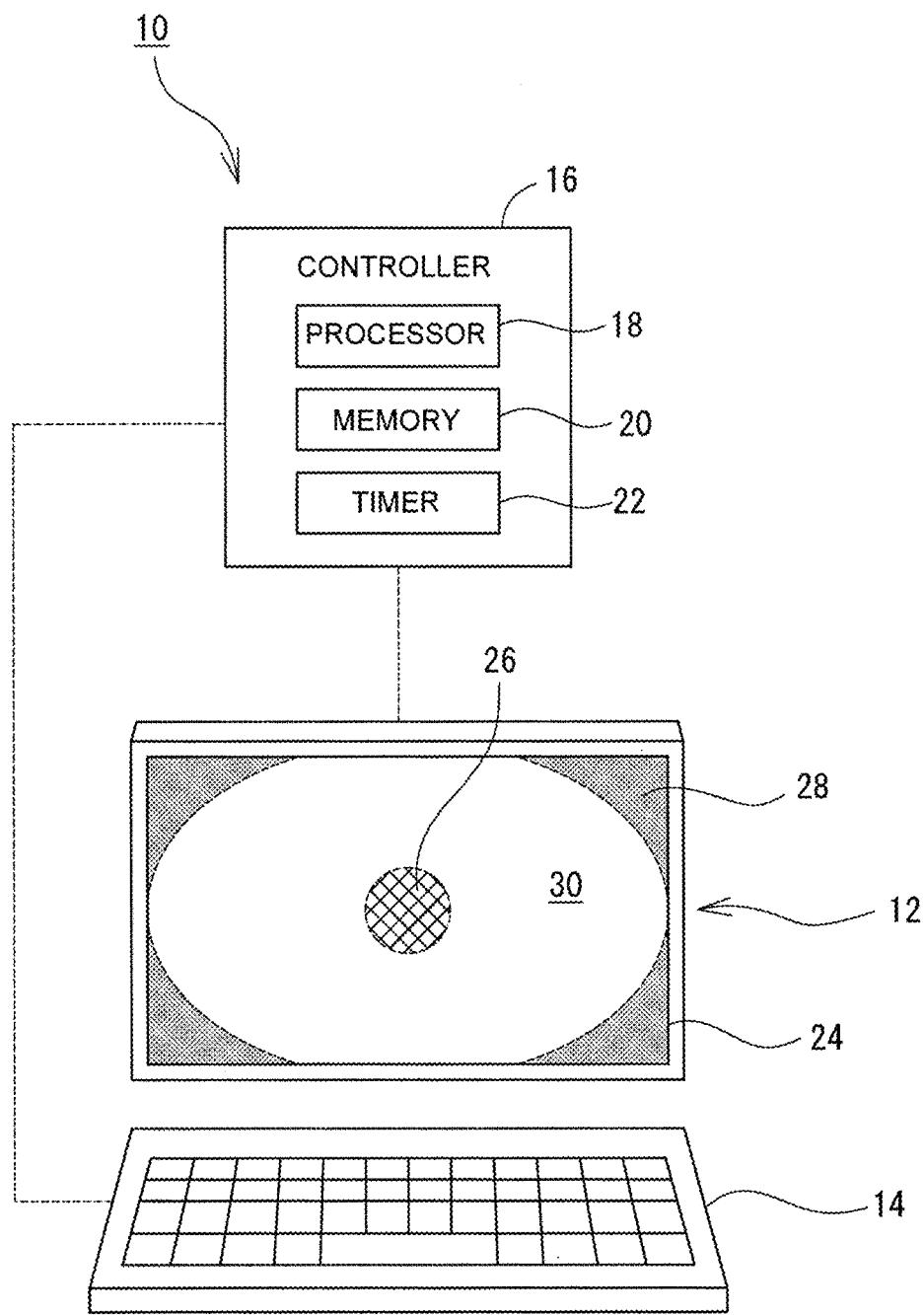
FIG. 1 is a diagram illustrating a physical configuration of an attention ability inspection device.
Figure 2:
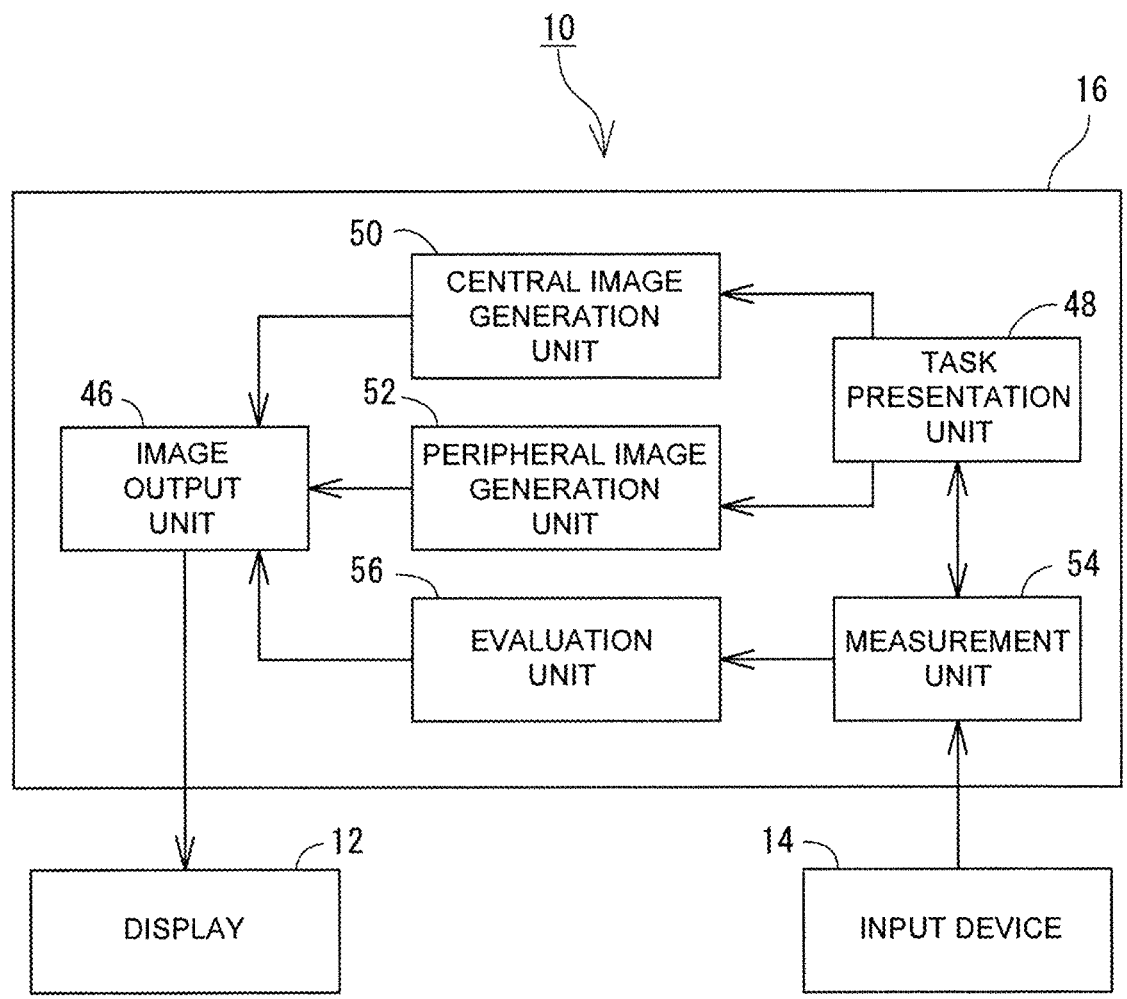
FIG. 2 is a block diagram illustrating a functional configuration of the attention ability inspection device.

Hereinbelow, a configuration of an attention ability inspection device 10 will be described with reference to the drawings. FIG. 1 is a diagram illustrating a physical configuration of the attention ability inspection device 10, and FIG. 2 is a block diagram illustrating a functional configuration of the attention ability inspection device 10. The attention ability inspection device 10 is a device that measures and inspects a visual attention ability of a subject.

Prior to description of a specific configuration of the attention ability inspection device 10, a visual attention ability to be inspected in the device 10 will be described. An information processing ability that a person can exhibit to process a target task (for example, a task of driving and operating a vehicle) varies depending on the visual attention ability of the person. In particular, in a case of driving an automobile, it is said that 90% of information to be processed is visual information, and the level of the visual attention ability is very important in processing a task of driving an automobile.

Such a visual attention ability greatly varies depending on the characteristics inherent in each person, the arousal level, the content of other tasks to be processed in parallel with the target task, and the like. For example, it is known that the visual attention ability is lowered when an arithmetic task or a memorizing task is being executed. It is also known that distribution of the visual attention ability in a visual field space is not uniform but is biased.

Figure 3:
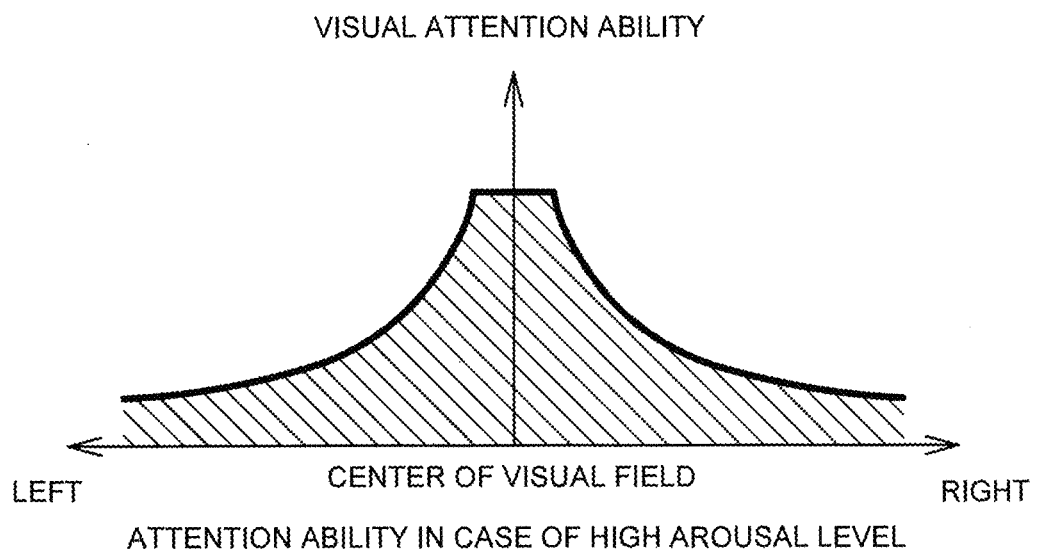
FIG. 3 provides graphs each illustrating an example of distribution of a visual attention ability in a space.
Figure 3:
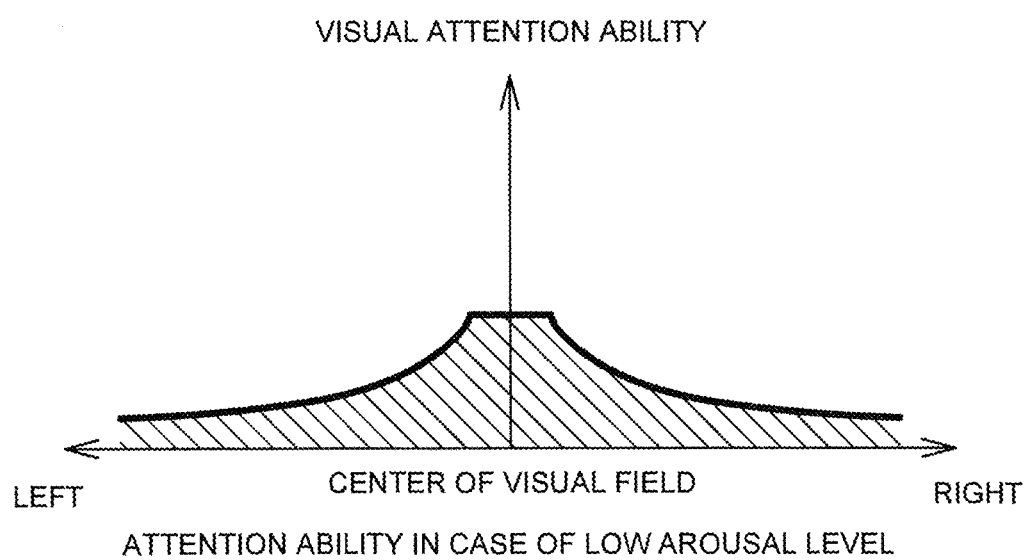
Figure 4:
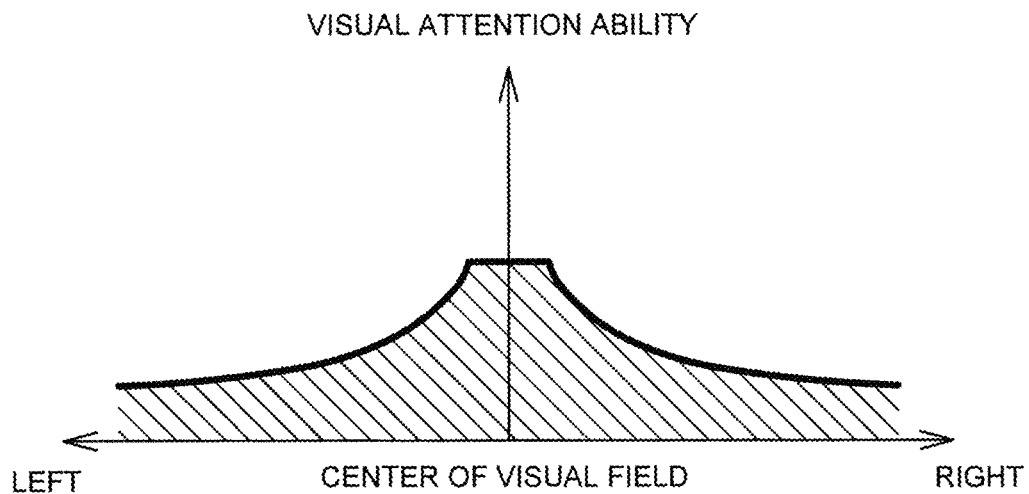
FIG. 4 provides graphs each illustrating an example of distribution of the visual attention ability in a case in which a non-visual task is executed in parallel.
Figure 4:
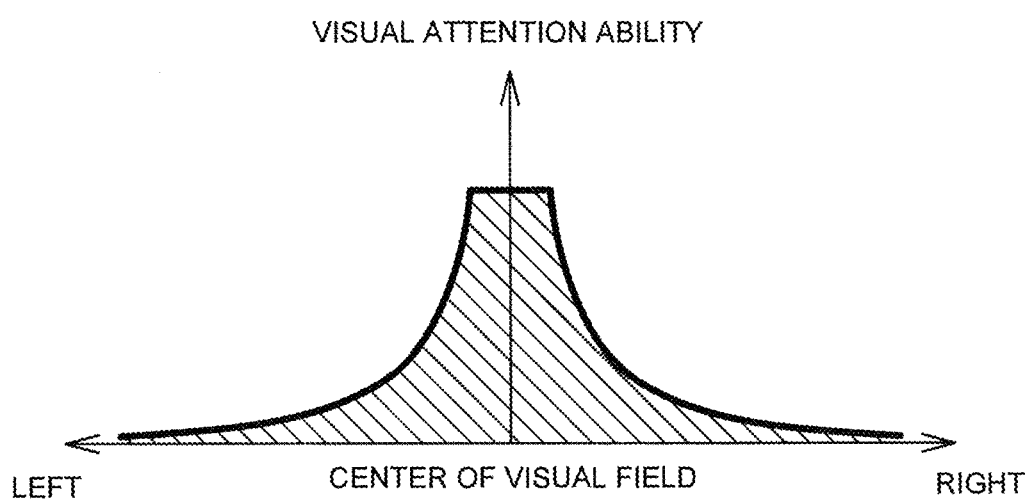

FIGS. 3 and 4 are graphs each illustrating an example of distribution of the visual attention ability in a space. In FIGS. 3 and 4, the vertical axis represents a level of the visual attention ability, and the horizontal axis represents a horizontal position in a visual field space. In general, while a person can exhibit a high visual attention ability at the center of his/her visual field, the visual attention ability at the periphery of the visual field is low. For example, while the person can recognize an image located at the center of the visual field accurately in a short time, he/she tends to take time to recognize an image located at the periphery of the visual field. As a result, as illustrated in FIG. 3, the visual attention ability has a mountain-shaped distribution in which the visual attention ability is the highest at the center of the visual field and is rapidly lowered from the center of the visual field toward the periphery of the visual field. Note that, hereinbelow, a visual attention ability at the center of the visual field is referred to as "a central vision attention ability", and a visual attention ability at the periphery of the visual field is referred to as "a peripheral vision attention ability".

The total amount of the visual attention ability can be expressed as the area of the hatched portion in the graph in FIG. 3. The total amount of the visual attention ability varies depending on the characteristics inherent in each person and the arousal level. For example, the lower the arousal level, the smaller the total amount of the visual attention ability. Also, the total amount of the visual attention ability of an elderly person is often lower than that of an adolescent or a middle-aged person. The upper part of FIG. 3 illustrates the visual attention ability of a person with a high arousal level, and the lower part of FIG. 3 illustrates the visual attention ability of a person with a low arousal level.

Also, a distribution form of the visual attention ability changes depending on the content of other tasks processed in parallel. For example, in a case in which a non-visual task such as a memorizing task or an arithmetic task is performed in parallel with a visual task that requires visual attention, a distribution form of the visual attention ability changes as compared with a case in which the visual task is performed so as not to be in parallel with any task. FIG. 4 provides graphs each illustrating an example of distribution of the visual attention ability in a case in which a non-visual task is executed in parallel. Specifically, the upper part of FIG. 4 is a graph illustrating distribution of a visual ability in a case in which a first non-visual task (for example, an arithmetic task) is processed in parallel, and the lower part is a graph illustrating distribution of a visual ability in a case in which a second non-visual task (for example, a memorizing task) is processed in parallel.

As is clear from the comparison between the upper part and the lower part of FIG. 4, even the same person has a different distribution form of the visual attention ability depending on the content of the non-visual task processed in parallel. For example, in a case in which the first non-visual task is processed in parallel, the central vision attention ability is likely to be lowered. On the other hand, in a case in which the second non-visual task is processed in parallel, the peripheral vision attention ability is likely to be lowered while the central vision attention ability is less likely to be lowered.

In this manner, the visual attention ability of a person is distributed in a mountain shape in a visual field space, and the distribution form changes depending on the content of the task processed in parallel. The attention ability inspection device 10 disclosed in the present description measures a level of the attention ability and distribution of the attention ability in the visual field space. This measurement result can be used for determining whether or not a subject has a visual attention ability suitable for execution of a target task (for example, a task of driving a vehicle), for example. Also, the attention ability inspection device 10 may be used for designing user interfaces of various devices. For example, a vehicle may be equipped with a voice interaction system that receives a voice command from a driver to the vehicle or makes an inquiry to the driver from the vehicle side by voice. The voice command or the inquiry content in the voice interaction system is required to have a difficulty level that does not interfere with the target task (that is, the task of driving a vehicle). The attention ability inspection device 10 may be used to determine whether or not the difficulty level of the voice command or the inquiry content in such a voice interaction system is appropriate.

Next, a configuration of the attention ability inspection device 10 that inspects such a visual attention ability will be described with reference to FIGS. 1 and 2. As illustrated in FIG. 1, the attention ability inspection device 10 physically includes a display 12 that displays an image, an input device 14 that receives an operation from a subject, and a controller 16.

The display 12 displays an image in a predetermined display area 24 and is a liquid crystal display, an organic EL display, or a projector, for example. In the present example, the display area 24 is roughly divided into a central region 26 in which a central graphic described below is displayed, a peripheral region 28 located further outside than the central region 26, and a middle region 30 interposed between the central region 26 and the peripheral region 28. Note that, in FIG. 1, to facilitate understanding, boundary lines of the respective regions 26, 28, and 30 are illustrated, and different patterns are applied to the respective regions 26, 28, and 30, but such boundary lines and patterns do not exist in the actual display area 24.

As will be described in detail below, in an inspection flow for inspecting an attention ability, the central graphic is displayed in the central region 26. Also, in the inspection flow, a central task of unsteadily changing the central graphic at a predetermined speed and a peripheral task of displaying a peripheral graphic in the peripheral region 28 are randomly presented.

The input device 14 receives an operation from the subject and includes at least one of a keyboard, a button, a joystick, a touch panel, a pedal, a mouse, and a microphone, for example. In the present example, the input device 14 is a keyboard including a space key and direction keys. As will be described in detail below, specific keys are associated with the central task and the peripheral task, respectively. Specifically, the space key is associated with the central task, and the direction keys are associated with the peripheral task. In the inspection flow, in a case in which the subject recognizes the presentation of the central task or the peripheral task, the subject operates the key associated with each task. Note that, in the present example, although the keyboard is used as the input device 14, the input device 14 is not limited to the keyboard and may be another operation tool such as a button, a joystick, a touch panel, a pedal, or a mouse, so long as an operation from the user can be received. Also, the input device 14 may be a microphone that receives a voice command. In this case, specific voice commands are associated with the central task and the peripheral task, respectively.

The controller 16 controls a display content in the display area 24 and determines the attention ability of the subject based on an operation content of the input device 14 performed by the subject in response to a displayed image. The controller 16 is a computer that physically includes a processor 18, a memory 20, and a timer 22. The "computer" also includes a microcontroller obtained by incorporating a computer system into one integrated circuit. Also, the processor 18 refers to a processor in a broad sense and includes a general-purpose processor (for example, a Central Processing Unit (CPU)) and a dedicated processor (for example, a Graphics Processing Unit (GPU), an Application Specific Integrated Circuit (ASIC), a Field Programmable Gate Array (FPGA), or a Programmable Logic Device). Also, the operation of the processor 18 described below may be performed not only by one processor but also by cooperation of a plurality of processors existing at physically separated positions. Similarly, the memory 20 does not need to be physically one element but may include a plurality of memories existing at physically separated positions. Also, the memory 20 may include at least one of a semiconductor memory (for example, a RAM, a ROM, or a solid state drive) and a magnetic disk (for example, a hard disk drive). The timer 22 measures passage of time. The timer 22 is driven in accordance with an instruction from the processor 18 and outputs a measurement result to the processor 18.

FIG. 2 illustrates a functional configuration of the controller 16 of the attention ability inspection device 10. A task presentation unit 48 determines whether or not the central task and the peripheral task need to be presented and outputs an instruction to present the central task to a central image generation unit 50 and an instruction to present the peripheral task to a peripheral image generation unit 52. The central image generation unit 50 generates an image to be displayed in the central region 26. In the central region 26, a central graphic 32 and a route graphic 44 are steadily displayed as described below. Also, in a case in which the instruction to present the central task is input, the central image generation unit 50 generates an image in which the central graphic 32 is unsteadily changed at a predetermined speed. The peripheral image generation unit 52 generates an image to be displayed in the peripheral region 28. Specifically, in a case in which the instruction to present the peripheral task is input, the peripheral image generation unit 52 generates an image of a peripheral graphic 34.

A measurement unit 54 measures a reaction time of the subject to the task. Specifically, the measurement unit 54 measures, as a central reaction time Rc, time from reception of the instruction to present the central task from the task presentation unit 48 to input of an operation corresponding to the central task. Similarly, the measurement unit 54 measures, as a peripheral reaction time Rp, time from reception of the instruction to present the peripheral task from the task presentation unit 48 to input of an operation corresponding to the peripheral task. The measurement unit 54 outputs the central reaction time Rc and the peripheral reaction time Rp acquired to an evaluation unit 56. Also, when an operation corresponding to the task is input, the measurement unit 54 outputs the input of the operation to the task presentation unit 48.

The evaluation unit 56 calculates an index indicating the central vision attention ability based on the central reaction time Rc and an index indicating the peripheral vision attention ability based on the peripheral reaction time Rp, and calculates the indexes as evaluation results. The evaluation unit 56 then generates an image indicating the calculated evaluation results and outputs the image to an image output unit 46. The image output unit 46 outputs the images generated in the central image generation unit 50, the peripheral image generation unit 52, and the evaluation unit 56 to the display 12.

Next, an inspection flow of the attention ability inspection performed in the attention ability inspection device 10 will be described. In the inspection flow, the central task or the peripheral task is presented in parallel with steady display in which the central graphic 32 is displayed in the central region 26 of the display area 24, and the reaction time of the subject to these tasks is measured.

Figure 5:
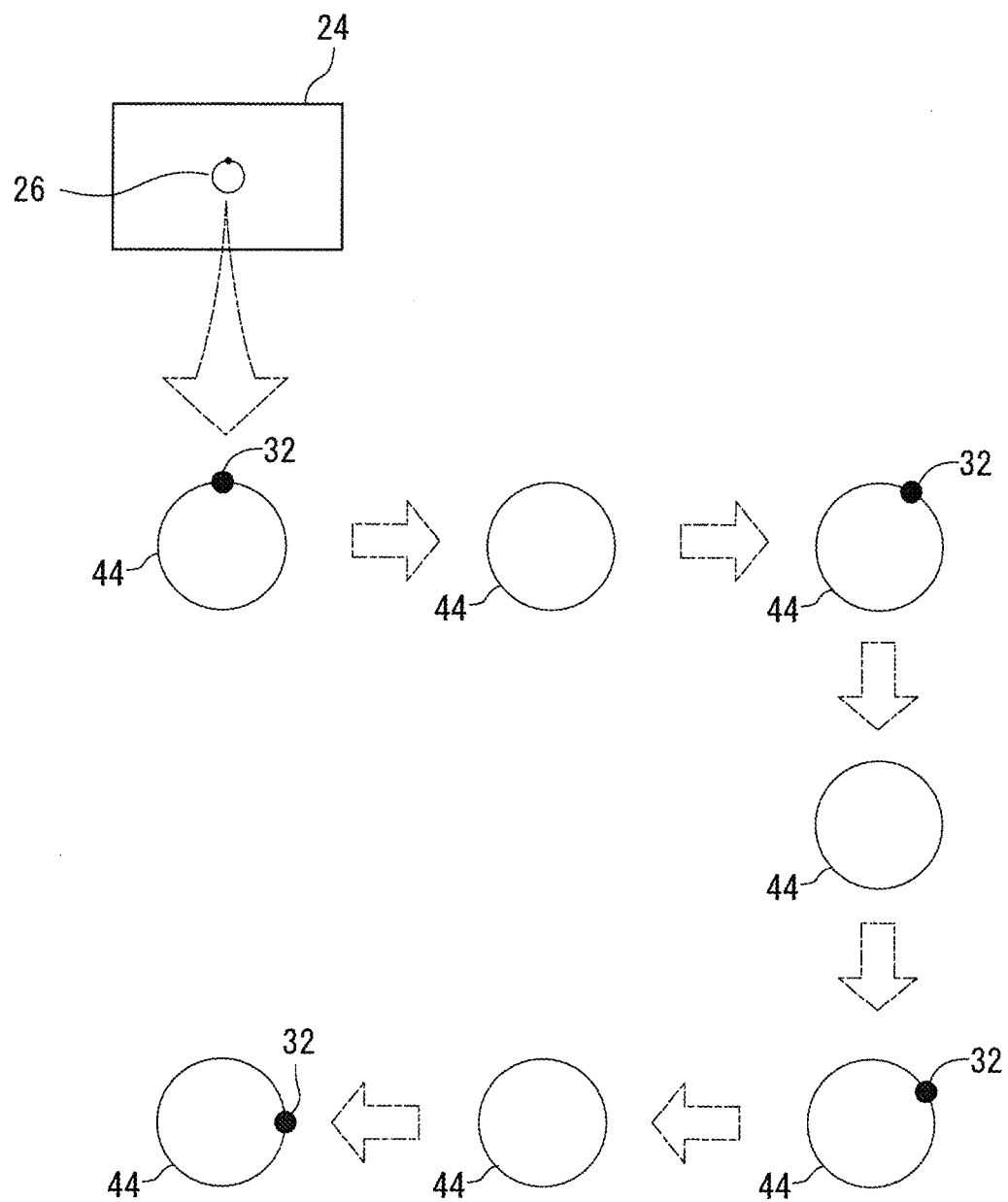
FIG. 5 is a diagram illustrating an example of steady display.

FIG. 5 is a diagram illustrating an example of the steady display. In the example in FIG. 5, the central graphic 32 is a small circle. In the steady display, the central graphic 32 (that is, the small black circle) moves at a constant speed along a predetermined traveling route while blinking. Note that, in the example in FIG. 5, the traveling route is a large circle having a center different from that of the small circle, which is the central graphic 32. In the steady display, a route graphic 44 indicating the traveling route is also displayed together with the central graphic 32.

Figure 6:
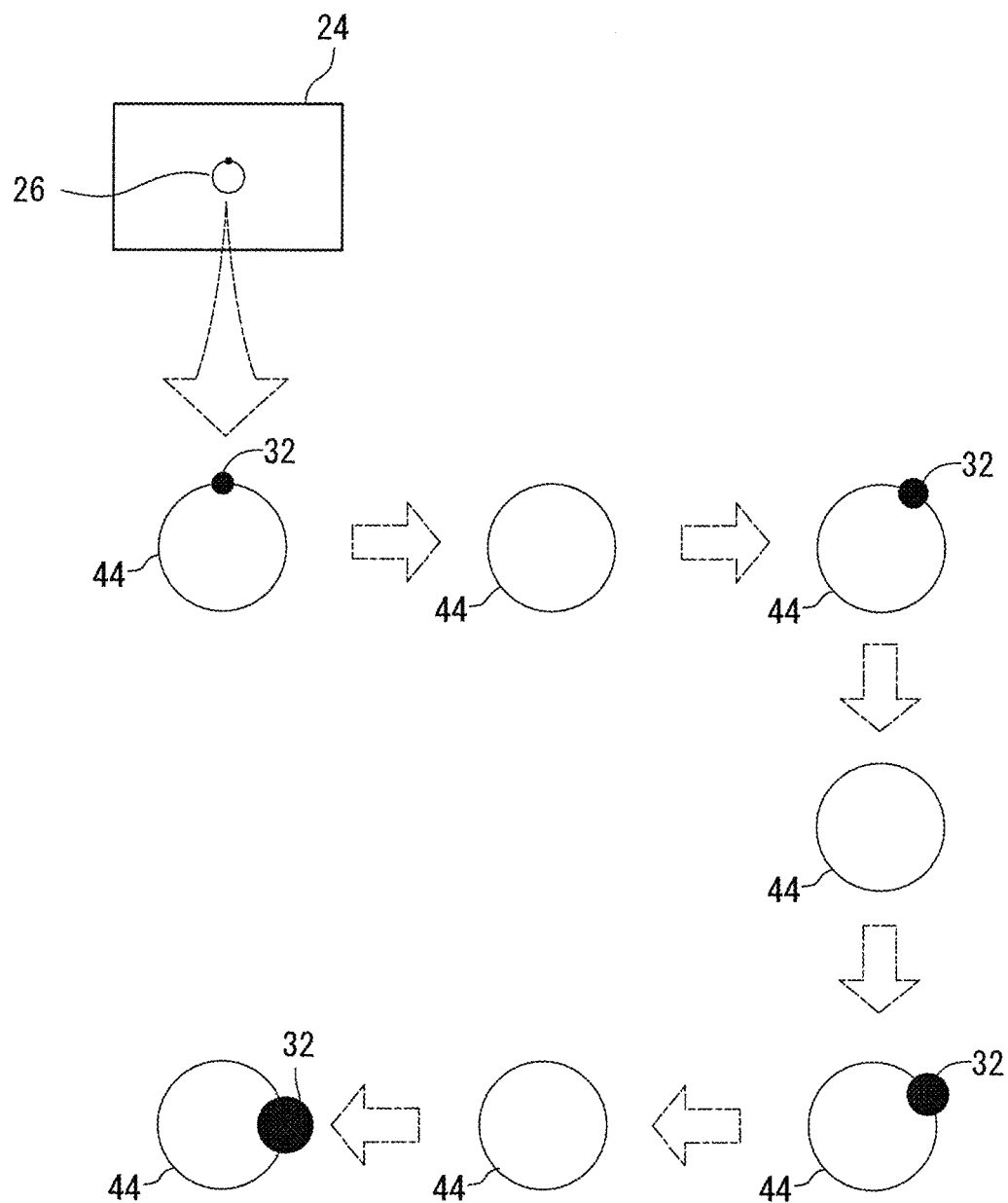
FIG. 6 is a diagram illustrating an example of a central task.

FIG. 6 is a diagram illustrating an example of the central task. The central task is to change the central graphic 32 unsteadily and at a predetermined speed. In the example in FIG. 6, the central task is to gradually expand the small circle, which is the central graphic 32. When recognizing occurrence of expansion of the central graphic 32, the subject operates a key (in the present example, the space key) associated with the central task.

Figure 7:
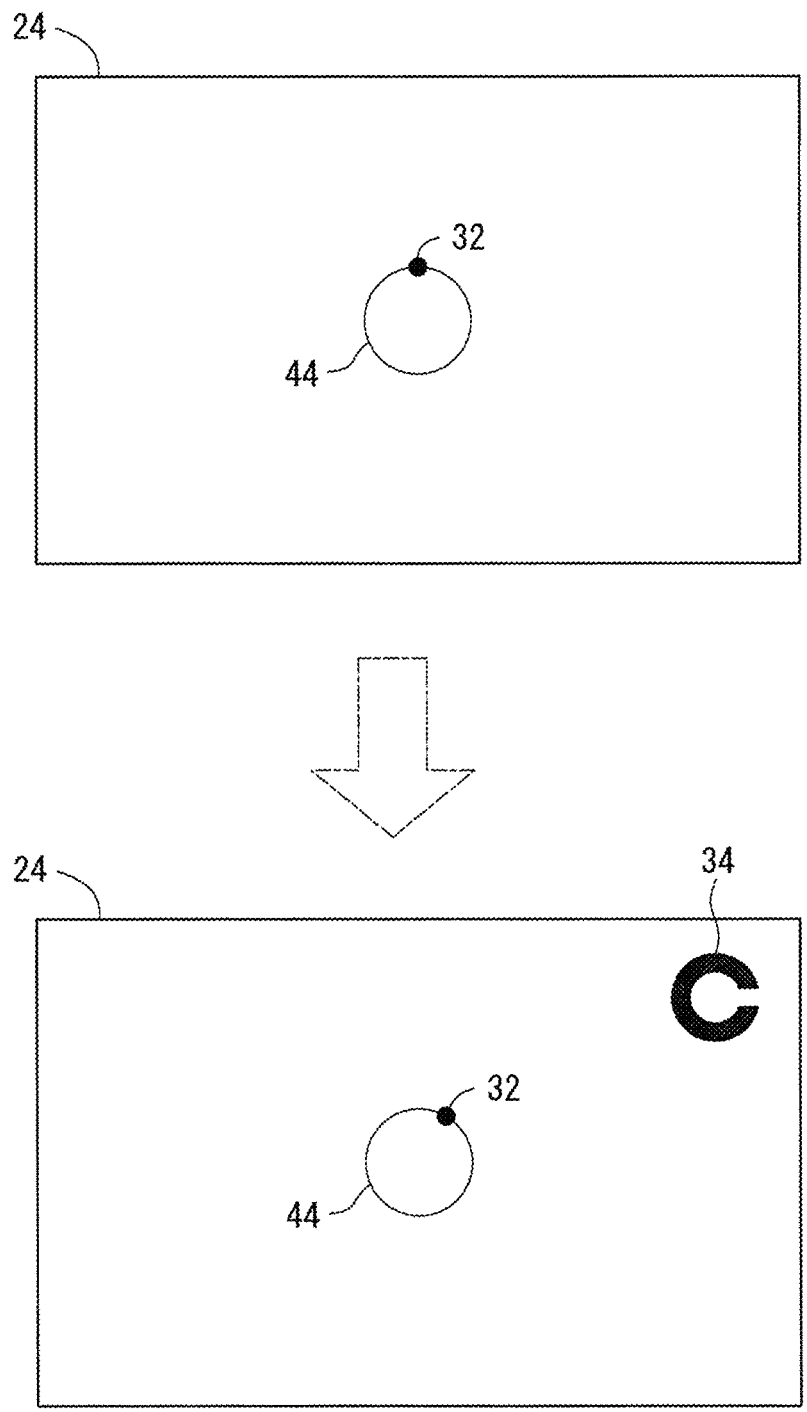
FIG. 7 is a diagram illustrating an example of a peripheral task.

FIG. 7 is a diagram illustrating an example of the peripheral task. The peripheral task is to display the peripheral graphic 34 in the peripheral region 28 of the display area 24. In the example in FIG. 7, the peripheral graphic 34 is a Landolt ring. The orientation of this Landolt ring; that is, the direction in which the ring is open, is randomly selected from the right and the left. The display position of the peripheral graphic 34 is also randomly selected in the peripheral region 28. However, in the present example, as illustrated in FIG. 1, a space in the peripheral region 28 that is sufficiently large as to enable the Landolt ring to be displayed is provided only at the four corners of the display area 24. Therefore, the peripheral graphic 34 (Landolt ring) is displayed at one corner randomly selected from the four corners of the display area 24. When recognizing the Landolt ring, the subject operates the direction key associated with the orientation of the Landolt ring.

In one inspection flow, an inspection set is repeated a plurality of times in parallel with the steady display. The inspection set that starts with presentation of either the central task or the peripheral task once and ends with reception of an operation corresponding to each task or timeout is regarded as one set. Hereinbelow, the inspection set in which the central task is presented is referred to as a "central inspection set", and the inspection set in which the peripheral task is presented is referred to as a "peripheral inspection set". The ratio of the presentation frequency of the central inspection set to the peripheral inspection set in one inspection flow is approximately 3:1, and the presentation frequency of the central inspection set is higher than the presentation frequency of the peripheral inspection set.

Figure 8:
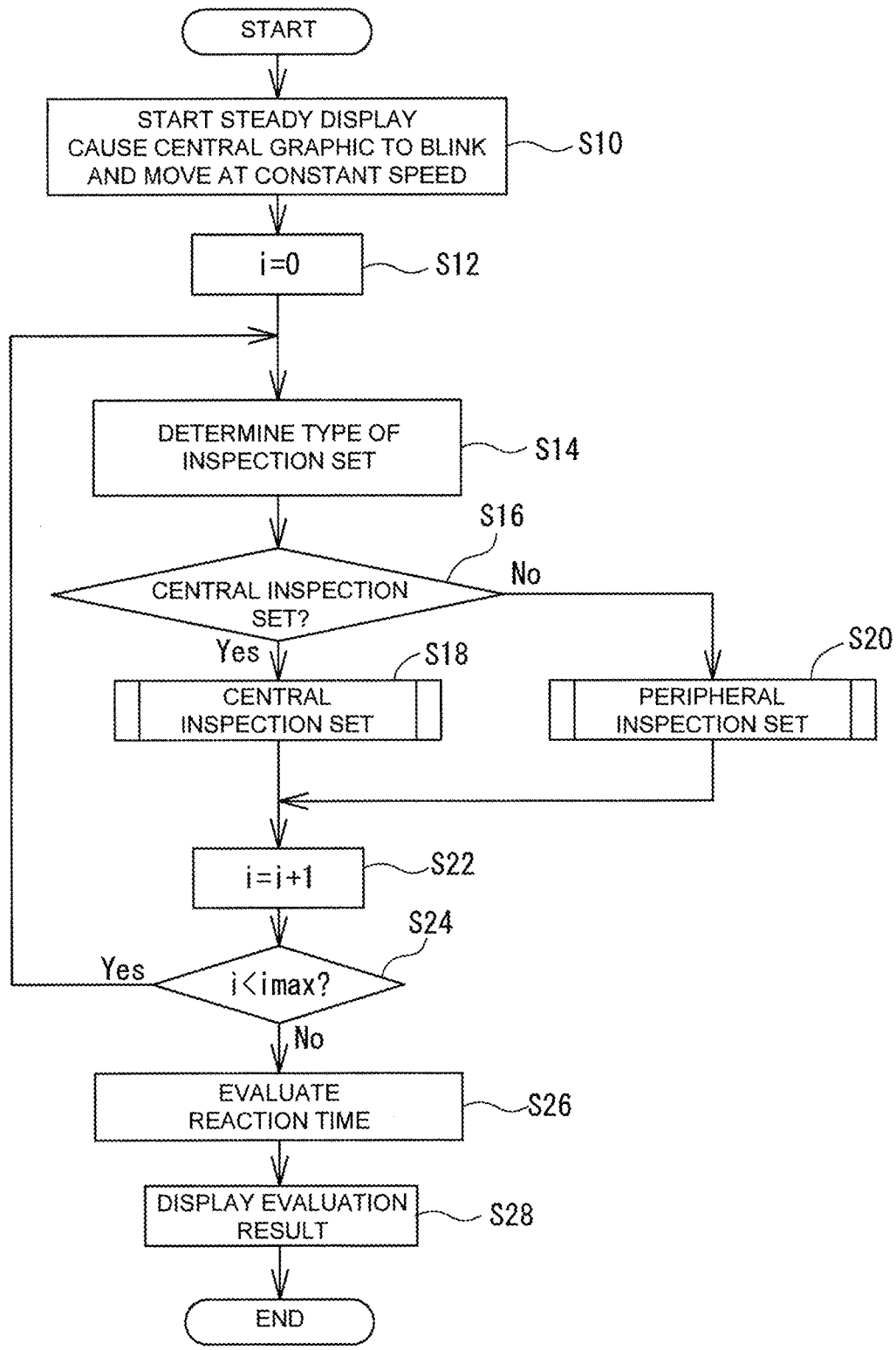
FIG. 8 is a flowchart illustrating an inspection flow performed in the attention ability inspection device.

FIG. 8 is a flowchart illustrating an inspection flow performed in the attention ability inspection device 10. In the inspection flow, the subject is arranged in front of the display area 24 and at a position away from the display area 24 by a predetermined distance in advance so that the relative positional relationship between the subject and the display area 24 becomes a predetermined relationship. When the relative positional relationship between the subject and the display area 24 becomes the predetermined relationship, the controller 16 starts the steady display (S10). That is, the route graphic 44 and the central graphic 32 are displayed in the central region 26 of the display area 24. In addition, the central graphic 32 is caused to blink periodically and to move along the route graphic 44 at a constant speed. Subsequently, the controller 16 sets a parameter i to an initial value 0 (S12).

Subsequently, the controller 16 determines the type of the inspection set to be performed (S14). This determination is performed so that the ratio of the presentation frequency of the central inspection set to the peripheral inspection set in one inspection flow is 3:1. For example, the controller 16 may randomly generate integer values of 1 to 4, and may perform the central inspection set in a case in which any value out of 1 to 3 is output and may perform the peripheral inspection set in a case in which a value 4 is output. As another method, a list in which an execution order of the central inspection set and the peripheral inspection set is recorded may be prepared in advance, and the type of the inspection set to be performed may be determined based on the list.

Figure 9:
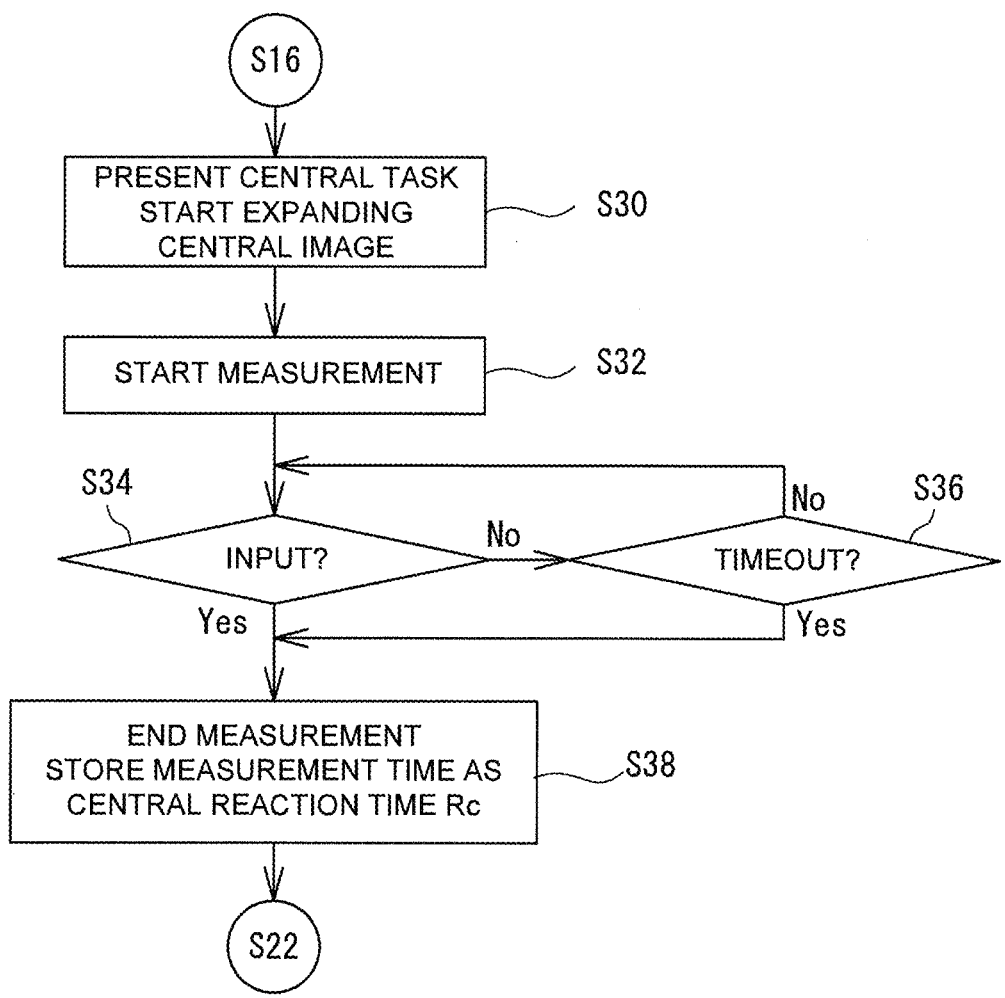
FIG. 9 is a chart illustrating a flow of a central inspection set.

In a case in which the central inspection set is selected in step S16 (Yes in S16), the controller 16 executes the central inspection set (S18). FIG. 9 is a chart illustrating a flow of the central inspection set. As illustrated in FIG. 9, in a case in which the central inspection set is selected, the controller 16 presents the central task (S30). That is, the central graphic 32 is gradually expanded. Also, the controller 16 starts measurement by the timer 22 at the same time as the start of the expansion (S32). Note that the start timing of the central task is randomly changed.

After the central task is presented, the controller 16 monitors whether or not a key (in the present example, the space key) associated with the central task has been input by the subject (S34). In a case in which the associated key is input (Yes in S34), the measurement by the timer 22 is ended, and the measurement time is stored in the memory 20 as the central reaction time Rc (S38). Note that, in a case in which a key not associated with the central task (for example, a numeric key) is input, the key is ignored. As another case, in a case in which an unassociated key is input, the processing may return to step S14, which is the step of determining the type of the inspection set, and the inspection set may be restarted from the beginning.

On the other hand, in a case in which the associated key is not input (No in S34), the controller 16 stands by until the measurement time reaches predetermined maximum standby time. In a case in which the measurement time reaches the maximum standby time without any key input, the controller 16 determines that the time has elapsed (Yes in S36), the processing proceeds to step S38, and the controller 16 stores the measurement time up to the present; that is, the maximum standby time, in the memory 20 as the central reaction time Rc. Note that, in a case in which the time has elapsed, the processing may return to step S14 instead of step S38, and the inspection set may be restarted from the beginning.

Figure 10:
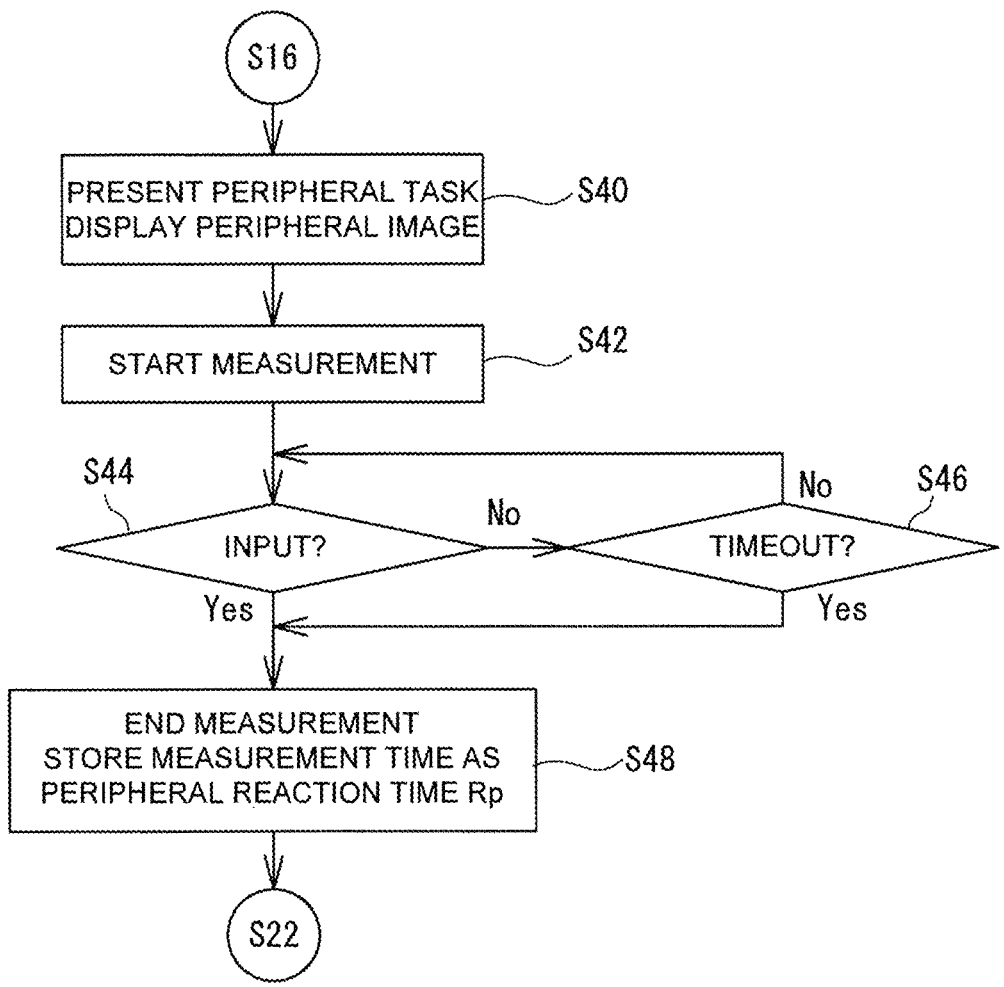
FIG. 10 is a chart illustrating a flow of a peripheral inspection set.

On the other hand, in a case in which the peripheral inspection set is selected in step S14 (No in S16), the controller 16 executes the peripheral inspection set (S20). FIG. 10 is a chart illustrating a flow of the peripheral inspection set. As illustrated in FIG. 10, in a case in which the peripheral inspection set is selected, the controller 16 presents the peripheral task (S40). That is, the peripheral graphic 34 is displayed in the peripheral region 28. More specifically, the controller 16 displays a Landolt ring facing to the right or left at one corner randomly selected from the four corners of the display area 24. Also, the controller 16 starts measurement by the timer 22 at the same time as the start of the display of the Landolt ring (S42). Note that the start timing of the peripheral task is randomly changed.

After the start of the display of the Landolt ring, the controller 16 monitors whether or not a key corresponding to the orientation of the Landolt ring is input by the subject (S44). That is, the controller 16 confirms whether or not the right arrow key has been input in a case in which the Landolt ring facing to the right is displayed and whether or not the left arrow key has been input in a case in which the Landolt ring facing to the left is displayed. In a case in which the associated key is input (Yes in S44), the measurement by the timer 22 is ended, and the measurement time is stored in the memory 20 as the peripheral reaction time Rp (S48). Note that, in a case in which a key not associated with the displayed Landolt ring is input, the key is ignored. Therefore, for example, in a case in which the left arrow key is input in a case in which the Landolt ring facing to the right is displayed, the processing proceeds to step S46, not to step S48. As another case, in a case in which an unassociated key is input, the processing may return to step S14, and the inspection set may be restarted from the beginning. Also, in a case in which the associated key is not input (No in S44), the controller 16 stands by until the measurement time reaches predetermined maximum standby time. In a case in which the measurement time reaches the maximum standby time without any key input, the controller 16 determines that the time has elapsed (Yes in S46), the processing proceeds to step S48, and the controller 16 stores the measurement time up to the present; that is, the maximum standby time, in the memory 20 as the peripheral reaction time Rp. Note that, in a case in which the time has elapsed, the processing may return to step S14 instead of step S48, and the inspection set may be restarted from the beginning.

In a case in which the central inspection set or the peripheral inspection set is ended, the processing proceeds to step S22 in FIG. 8, and the controller 16 increments the parameter i (S22). Subsequently, the controller 16 confirms whether or not the parameter i has reached a predetermined target number of times imax (S24). In a case of i<imax (Yes in S24), the processing returns to step S14, and the controller 16 executes S14 to S22 again. On the other hand, in a case of i=imax (No in S24), the controller 16 evaluates the attention ability of the subject based on the reaction times Rc and Rp acquired so far (S26). Specifically, the controller 16 calculates a statistical value of the central reaction times Rc acquired in the plurality of central inspection sets as an evaluation index for the central vision attention ability. Note that the statistical value used here only has to be any value indicating a tendency among the plurality of central reaction times Rc such as an average value, a minimum value, and an intermediate value. Similarly, the controller 16 calculates a statistical value (for example, an average value, a minimum value, or an intermediate value) of the peripheral reaction times Rp acquired in the plurality of peripheral inspection sets as an evaluation index for the peripheral vision attention ability. Then, when the acquired display result is displayed in the display area 24 (S28), the inspection flow ends.

Next, effects of the inspection flow performed in the attention ability inspection device 10 will be described. In the present example, the central task and the peripheral task are randomly presented, and the reaction times of the subject to the central task and the peripheral task are measured. This makes it possible to obtain both the central vision attention ability and the peripheral vision attention ability and thus to measure the distribution of the attention abilities in the visual field space.

Also, in the present example, a change of the graphic is set as the central task, and an appearance of the graphic is set as the peripheral task. Here, in general, the change of the graphic is more difficult to find than the appearance of the graphic. By setting the phenomenon that is difficult to find as the central task, it is possible to measure both the central vision attention ability and the peripheral vision attention ability while the line of sight of the subject is kept in an appropriate direction. That is, in order to appropriately measure both the central vision attention ability and the peripheral vision attention ability, the line of sight of the subject needs to be oriented in the direction of the central region 26. In the present example, since the "change of the graphic", which is difficult to find, is presented in the central region 26, the subject naturally continues to orient the line of sight in the direction of the central region 26 in an attempt to find the change. As a result, both the central vision attention ability and the peripheral vision attention ability can be measured appropriately.

Also, in the present example, the central graphic 32 is caused to blink periodically. In the case of such a configuration, in order to find a change of the central graphic 32, the subject needs to temporarily memorize in the brain memory the central graphic 32 displayed before extinction and compare the central graphic 32 displayed again with the central graphic 32 memorized in the brain memory. Therefore, the central vision attention ability measured in the present example reflects the state of the brain memory. Here, in a task of driving an automobile or the like, the brain memory needs to act appropriately. Therefore, as in the present example, by measuring the central vision attention ability reflecting the state of the brain memory, the ability required for the driving task or the like can be measured more accurately.

Also, in the present example, the central graphic 32 is moved at a constant speed. In the case of such a configuration, the subject can predict movement of the central graphic 32. In the case of such a configuration, in order to find a change of the central graphic 32, the subject needs to predict a future image of the central graphic 32, temporarily memorize the image in the brain memory, and compare the predicted image of the central graphic 32 memorized with the central graphic 32 displayed currently. Therefore, in this case, the central vision attention ability measured in the present example reflects the state of the brain memory, and the ability required for the driving task or the like can be measured more accurately.

Also, as is clear from the above description, in the present example, the operation corresponding to the central task and the operation corresponding to the peripheral task are different from each other. With such a configuration, the reaction to the central task and the reaction to the peripheral task can be distinguished clearly and acquired. For example, depending on the state of the subject, although a peripheral task is being presented, the subject may not be aware of the peripheral task and may erroneously recognize that a central task is being presented. In this case, in a case in which the operation to the central task and the operation to the peripheral task are the same, it is not possible to distinguish whether the subject is aware of the peripheral task or erroneously recognizes that the central task is being presented. By setting different operations corresponding to the central task and the peripheral task, respectively, as in the present example, such a problem can be avoided.

Figure 11:
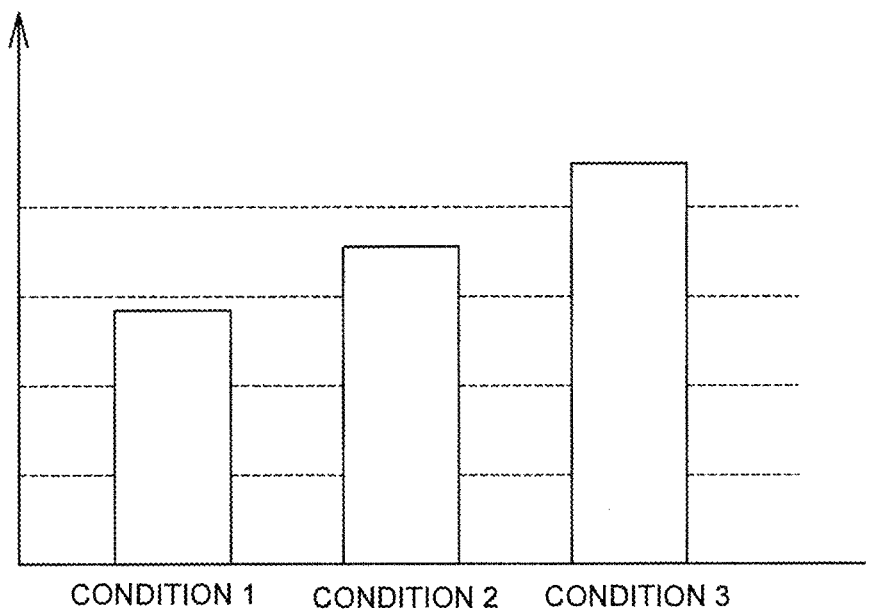
FIG. 11 is a graph illustrating a central reaction time obtained in the inspection flow.
Figure 12:
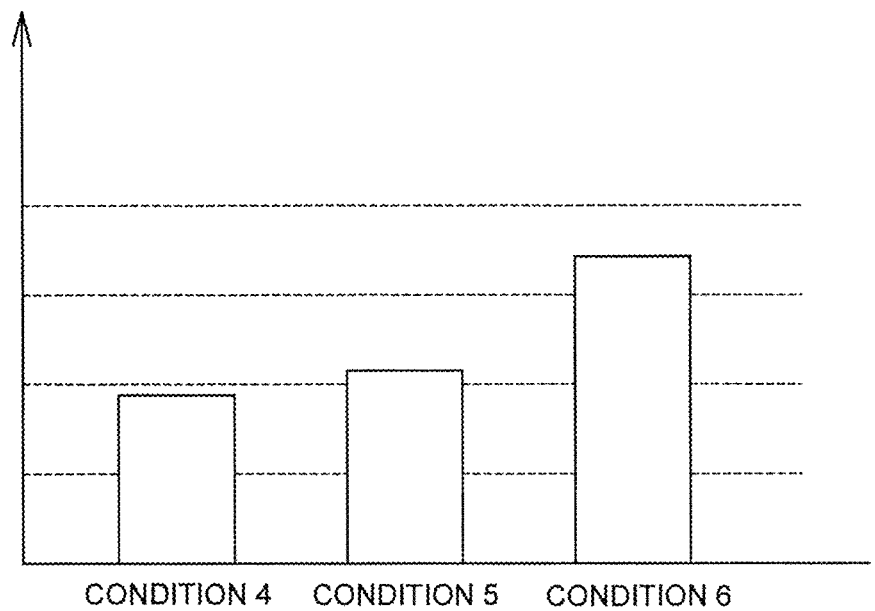
FIG. 12 is a graph illustrating a peripheral reaction time obtained in the inspection flow.

FIGS. 11 and 12 are graphs illustrating an example of an inspection result obtained in the above-described inspection flow. FIG. 11 is a graph illustrating the central reaction time Rc. In FIG. 11, condition 1 indicates the central reaction time Rc in a case in which there is no other task to process in parallel with the above inspection flow. Also, condition 2 indicates the central reaction time Rc in a case in which an arithmetic task of sequentially subtracting 2 from a result obtained by the subtraction beginning from 100 is performed in parallel with the above inspection flow. Further, condition 3 indicates the central reaction time Rc in a case in which an arithmetic task of sequentially subtracting 7 from a result obtained by the subtraction beginning from 100 is performed in parallel with the above inspection flow. As is apparent from FIG. 11, as the difficulty level of the arithmetic task performed in parallel is higher, the central reaction time Rc is longer, and the central vision attention ability is further lowered. That is, with the inspection method according to the present example, it is apparent that the influence of the arithmetic task on the attention ability can be measured.

FIG. 12 is a graph illustrating the peripheral reaction time Rp. In FIG. 12, condition 4 indicates the peripheral reaction time Rp in a case in which there is no other task to process in parallel with the above inspection flow. Also, condition 5 indicates the peripheral reaction time Rp in a case in which a memorizing task of uttering the number provided immediately before among the numbers randomly given is performed in parallel with the above inspection flow. Further, condition 6 indicates the peripheral reaction time Rp in a case in which a memorizing task of uttering the number provided one time before among the numbers randomly given is performed in parallel with the above inspection flow. As is apparent from FIG. 12, as the difficulty level of the memorizing task performed in parallel is higher, the peripheral reaction time Rp is longer, and the peripheral vision attention ability is further lowered. That is, with the inspection method according to the present example, it is apparent that the influence of the memorizing task on the attention ability can be measured.

Figure 13A:
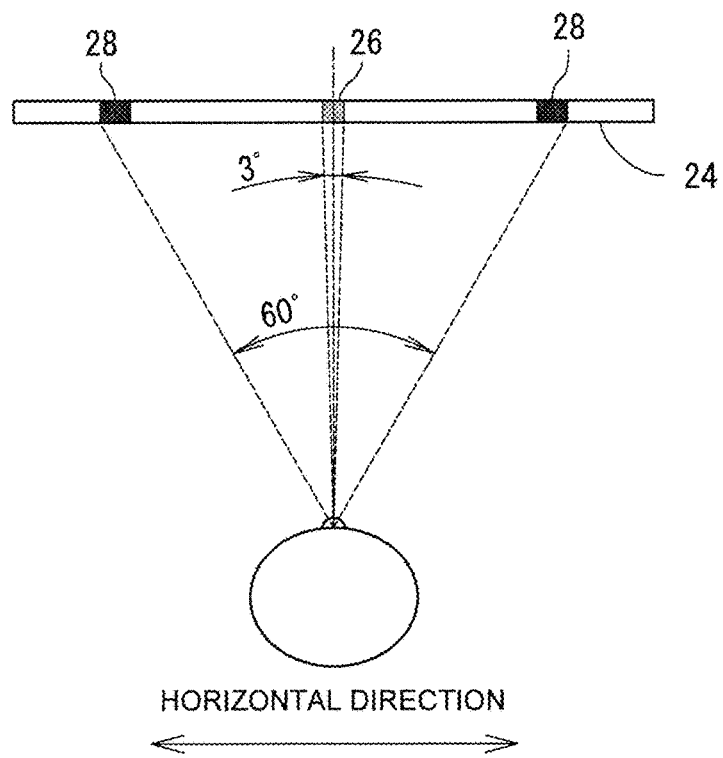
FIG. 13A is a diagram describing horizontal ranges of a central region and a peripheral region.
Figure 13B:
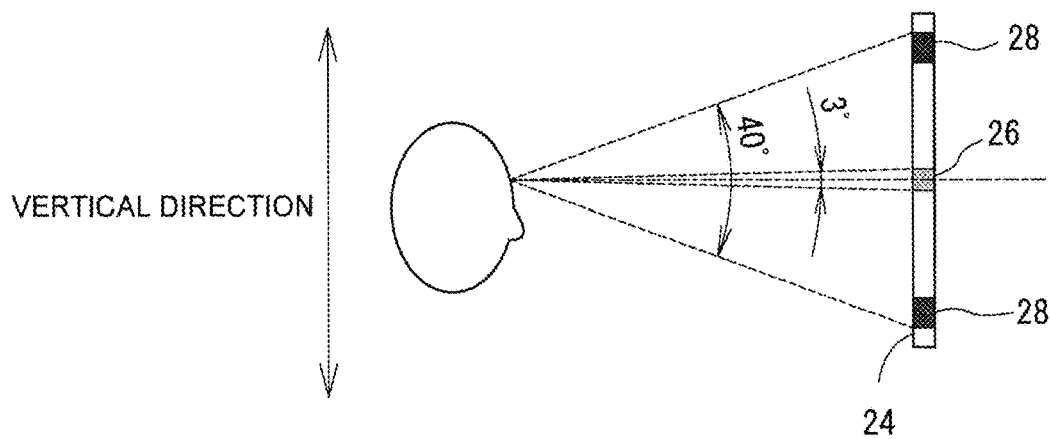
FIG. 13B is a diagram describing vertical ranges of the central region and the peripheral region.

Next, ranges of the central region 26 and the peripheral region 28 will be described with reference to FIGS. 13A and 13B. FIG. 13A is a diagram describing horizontal ranges of the central region 26 and the peripheral region 28, and FIG. 13B is a diagram describing vertical ranges of the central region 26 and the peripheral region 28. As described above, in the present example, the central graphic 32 is displayed in the central region 26, and the peripheral graphic 34 is displayed in the peripheral region 28. Among them, the central region 26 is set in a region captured by the foveae; specifically, a region in a range of 3 degrees of vision. Also, the peripheral region 28 is set in the vicinity of the boundary of an effective visual field required.

Specifically, it is generally said that the human visual field; that is, the range that can be viewed without moving the eyes is about 200 degrees in the horizontal direction and about 130 degrees in the vertical direction. In this visual field, an image in the range of 3 degrees of vision can be captured by the foveae of the eyeballs, and the image can be processed with high resolution. In the present example, the range of 3 degrees of vision is set as the central region 26, and the central graphic 32 is moved within the range of 3 degrees of vision.

Also, the peripheral region 28 is set based on the effective visual field required. The effective visual field is a region in which information processing can be performed simultaneously with viewing. The effective visual field required differs depending on the content of a task to be performed, and for example, in a case in which a task of driving an automobile is to be performed appropriately, it is said that an effective visual field of about 60 degrees in the horizontal direction and about 40 degrees in the vertical direction is required. Therefore, in a case in which an attention ability for the task of driving an automobile is measured, the peripheral region 28 is set based on the boundary of the effective visual field of 60 degrees in the horizontal direction and 40 degrees in the vertical direction. Specifically, a range surrounded by the boundary of the effective visual field and a line obtained by offsetting the boundary inward by a predetermined distance is set as the peripheral region 28. The offset distance only has to be set in accordance with the size of the peripheral graphic 34, and the size of the peripheral graphic 34 only has to be set based on the minimum visual acuity of the subject. For example, in a case in which an attention ability for the task of driving an automobile is inspected, it is assumed that the subject has visual acuity necessary for obtaining a driver's license. In Japan, the visual acuity of both eyes is required to be 0.7 or more to obtain a driver's license, and thus the size of the peripheral graphic 34 is a size that can be recognized with the visual acuity of both eyes of 0.7.

Note that, in the example in FIG. 1, due to the size of the display area 24, a space in which the peripheral graphic 34 can be displayed in the peripheral region can be secured only at the four corners of the display area 24. Therefore, in the present example, the peripheral graphic 34 is displayed only at the four corners of the display area 24. However, in a case in which a space in which the peripheral graphic 34 can be displayed in the peripheral region can be secured also in regions located in the vertical direction and the horizontal direction of the central region 26, the peripheral graphic 34 may be displayed in such a space.

Also, in a case in which the relative positional relationship between the display area 24 and the subject changes, the range of 3 degrees of vision in the display area 24; that is, the range suitable for the central region 26, changes. In order to prevent such a change of the range suitable for the central region 26, the position of the subject is adjusted so that the relative positional relationship between the display area 24 and the subject is always stable when the attention ability is inspected.

Next, the central task and the peripheral task will be described. In the present example, the central graphic 32 is expanded as the central task. However, the central task may be in another form, so long as the central graphic 32 is unsteadily changed at a predetermined speed. For example, the central task may be any of a change in size, a change in color, a change in luminance, a change in moving speed, a change in shape of the central graphic 32, and a combination thereof. Therefore, the central task may be to change the color of the central graphic 32 from black to red or to change the shape of the central graphic 32 from a circle to a rhombus, for example. Further, the central task may be to increase the luminance while expanding the central graphic 32, for example. Note that, as is apparent from the above description, the central graphic 32 (that is, the small black circle) changes (that is, blinks and moves) even in the steady display. The change that occurs in the steady display is a cyclic change in which the state is returned to the original state with the lapse of time without being reset. That is, the change that occurs in the steady display is a cyclic change in which the lighting state and the extinction state are repeated and a change in which the central graphic 32 cyclically moves along one large circle. On the other hand, the change that occurs in the central task is a non-cyclic change in which the state of the central graphic 32 gradually shifts from a first state (for example, a state before expansion) to a second state (for example, a state after complete expansion) until being reset.

Also, In the present example, although the central graphic 32 is a small black circle, the central graphic 32 may be in another shape. However, in the present example, the central graphic 32 moves along the route graphic 44 while blinking, and the relative position of the central graphic 32 with respect to the route graphic 44 gradually changes. As the central graphic 32, a graphic is set whose appearance impression hardly changes even when the relative position of the central graphic 32 with respect to the route graphic 44 changes. For example, in a case where a certain figure is rotated by 360/n degrees and completely overlaps the original figure, n is referred to as the order of rotational symmetry. In general, as the order n of rotational symmetry is higher, the appearance impression is less likely to change even when the relative position changes. Therefore, as the central graphic 32, a rotationally symmetric graphic having the degree n of 6 or more may be set, for example.

Also, the peripheral task may be appropriately changed in other respects so long as the peripheral graphic 34 is displayed in the peripheral region 28. For example, the peripheral graphic 34 is not limited to the Landolt ring but may be of another shape such as an arrow graphic or a polygon. Note that the peripheral task may be a task that requires not only grasping the presence or absence of the peripheral graphic 34 in the peripheral region 28 but also information processing for interpreting the meaning of the peripheral graphic 34. For this purpose, a plurality of types of peripheral graphic 34 used in the peripheral task may be prepared, and different operations may be caused to correspond to the respective types. For example, three types of graphic of a triangle, a quadrangle, and a pentagon may be prepared as the peripheral graphic 34, and input of a numeric key indicating the number of sides of each polygon may be set as the corresponding operation.

Meanwhile, in the present example, the ratio of the presentation frequency of the central task to the peripheral task is set to 3:1, and the presentation frequency of the central task is set to be higher than the presentation frequency of the peripheral task. The reason for this is that, in the driving task as a target task, the central vision attention ability is more important than the peripheral vision attention ability. In addition, by setting the presentation frequency of the central task to be higher, the subject tries to maintain a state in which the line of sight of the subject is oriented to the central region 26 so that the subject can deal with the central task rather than the peripheral task. As a result, since the line of sight of the subject can be maintained in an appropriate state, the central vision attention ability and the peripheral vision attention ability can be measured more accurately. The ratio of the presentation frequency of the central task to the peripheral task may be appropriately changed in accordance with the purpose of the attention ability inspection.

Also, in the present example, the total number of inspection sets included in one inspection flow is set to a predetermined target number of times imax, and the ratio of the presentation frequency of the central task to the peripheral task is set to 3:1. In a case in which the target number of times imax and the ratio of the presentation frequency are fixed values, the subject may be able to predict in advance the type of the next task to occur, and the attention ability may not be able to be measured accurately. For example, suppose that the target number of times imax is set to 12, and that the ratio of the presentation frequency is set to 3:1. In this case, in a case in which the central task is presented nine times and the peripheral task is presented two times at the time when the inspection set is executed eleven times, the subject can easily predict that the last inspection set is the peripheral inspection set and may actively direct attention to the peripheral region. In such a case, the peripheral vision attention ability cannot be measured accurately. Therefore, in order to make it difficult to predict the type of the inspection set to be performed next, at least one of the ratio of the presentation frequency and the target number of times imax may be randomly changed.

Also, each of the configurations described so far is illustrative only, and other configurations may be appropriately changed so long as at least one of the central task and the peripheral task is randomly presented in parallel with the steady display, the reaction time from the presentation of the task to the input of the corresponding operation is measured, and the attention ability of the subject is measured based on the measured reaction time. For example, in the above example, although the central task and the peripheral task are not presented simultaneously, the central task and the peripheral task may be presented in parallel. For example, after the expansion of the central graphic 32 is started, the peripheral graphic 34 may be displayed in the peripheral region 28 before the operation corresponding to the central task is input.

Also, in the above example, although the central graphic 32 is moved at a constant speed while blinking as the steady display, at least one of the blinking and the constant speed movement may be omitted. Also, although a case in which the display area 24 is a single continuous area has been described above as an example, the display area 24 may be divided into a plurality of areas. For example, a plurality of displays (for example, a display of a smartphone) may be prepared, one of the displays may be arranged at a position covering the central region 26, and the remaining displays may be arranged at positions covering the peripheral region 28. This configuration eliminates the need for the large-screen display 12, and the attention ability inspection device 10 can thus be provided relatively inexpensively. The attention ability inspection device 10 may be mounted on a vehicle. For example, the central graphic 32 may be displayed on a meter display provided on an instrument panel, and the peripheral graphic 34 may be displayed on a side mirror instead of a blind spot monitoring indicator. With such a configuration, an attention ability necessary for a task of driving the vehicle can be inspected easily before starting driving.

Also, the attention ability inspection technology disclosed in the present description may be used not only for determination of the presence or absence of the automobile driving ability and the quality determination of the user interface but also for other purposes. For example, the technology disclosed in the present description may be used for an inspection of the influence on an attention ability of drinking alcohol or taking a drug acting on the mind (for example, an antidepressant). Further, the technology disclosed in the present description may be used for detection of a visual field defect caused by glaucoma or the like.

REFERENCE SIGNS LIST

10 attention ability inspection device
12 display
14 input device
16 controller
18 processor
20 memory
22 timer
24 display area
26 central region
28 peripheral region
30 middle region
32 central graphic
34 peripheral graphic
44 route graphic
46 image output unit
48 task presentation unit
50 central image generation unit
52 peripheral image generation unit
54 measurement unit
56 evaluation unit

The invention claimed is:

1. An attention ability inspection device, comprising:
a display configured to display an image in a display area;
an input device configured to receive an operation from a subject; and
a controller configured to
  control a display content in the display area, and
  determine an attention ability of the subject based on an operation content of the input device performed by the subject in response to a displayed image on the display, wherein
the controller is configured to
  cause the display to display a central graphic in a central region of the display area in steady display, wherein, in the steady display, the central graphic is caused to blink periodically while moving at a constant speed along a predetermined traveling route in the central region without relevance to an operation from the subject,
  randomly present at least one of
    (i) a central task of unsteadily changing the central graphic at a predetermined speed, or
    (ii) a peripheral task of displaying a peripheral graphic in a peripheral region of the display area in parallel with the steady display,
  measure, as reaction time, time from presentation of the central task or the peripheral task to reception of a predetermined operation from the subject that has recognized the presentation, and evaluate the attention ability of the subject based on the reaction time, and the central task includes gradual expansion of the central graphic.

2. The attention ability inspection device according to claim 1, wherein the controller is configured to evaluate the attention ability of the subject at a center of a visual field based on the reaction time to the central task, and evaluate the attention ability of the subject at a periphery of the visual field based on the reaction time to the peripheral task.

3. The attention ability inspection device according to claim 1, wherein the controller is configured to perform a plurality of inspection sets by repeating an inspection set a plurality of times in one inspection flow, wherein the inspection set that starts with the presentation of either the central task or the peripheral task once and ends with the reception of the predetermined operation or timeout is regarded as one set of the plurality of inspection sets, and evaluate the attention ability of the subject based on the reaction time obtained in each of the plurality of inspection sets.

4. The attention ability inspection device according to claim 3, wherein a number of times of presentation of the central task is greater than a number of times of presentation of the peripheral task in the one inspection flow.

5. The attention ability inspection device according to claim 3, wherein the controller is configured to randomly change a timing from start of the inspection set to the presentation of the central task or the peripheral task.

6. The attention ability inspection device according to claim 3, wherein the controller is configured to change a ratio of a number of times of presentation of the central task to a number of times of presentation of the peripheral task in the one inspection flow.

7. The attention ability inspection device according to claim 1, wherein the predetermined operation includes a first operation corresponding to the central task, and a second operation corresponding to the peripheral task and different from the first operation.

8. The attention ability inspection device according to claim 7, wherein the peripheral graphic is a Landolt ring graphic, and the second operation is an operation of indicating a direction in which the Landolt ring graphic is open.

9. An attention ability inspection method, comprising:

displaying a central graphic in a central region of a display area of a display in a steady display, wherein, in the steady display, the central graphic is caused to blink periodically while moving at a constant speed along a predetermined traveling route in the central region without relevance to an operation from a subject;

randomly presenting at least one of (i) a central task of unsteadily changing the central graphic at a predetermined speed, or (ii) a peripheral task of displaying a peripheral graphic in a peripheral region of the display area in parallel with the steady display;

measuring, as reaction time, time from presentation of the central task or the peripheral task to reception of a predetermined operation from the subject that has recognized the presentation; and evaluating an attention ability of the subject based on the reaction time, wherein the central task includes gradual expansion of the central graphic.

10. The attention ability inspection device according to claim 1, wherein the controller is configured to, in response to a relative positional relationship between the subject and the display area becoming a predetermined relationship, set a range of 3 degrees of vision of the subject as the central region in the display area, and set (i) a range surrounded by a boundary of an area of 60 degrees in a horizontal direction and 40 degrees in a vertical direction from a center of a line of sight of the subject, and (ii) a line obtained by offsetting the boundary inward by a predetermined distance, as the peripheral region in the display area.

11. The attention ability inspection device according to claim 1, wherein the display area is divided into (i) the central region, (ii) the peripheral region located further outside than the central region, and (iii) a middle region interposed between the central region and the peripheral region, the central graphic is displayed only in the central region, the peripheral graphic is displayed only in the peripheral region, and neither the central graphic nor the peripheral graphic is displayed in the middle region.

12. The attention ability inspection method according to claim 9, wherein the evaluating of the attention ability includes evaluating the attention ability of the subject at a center of a visual field based on the reaction time to the central task, and evaluating the attention ability of the subject at a periphery of the visual field based on the reaction time to the peripheral task.

13. The attention ability inspection method according to claim 9, wherein in the randomly presenting of said at least one of the central task or the peripheral task, a plurality of inspection sets is performed by repeating an inspection set a plurality of times in one inspection flow, wherein the inspection set, that starts with the presentation of either the central task or the peripheral task once and ends with the reception of the predetermined operation or timeout, is regarded as one set of the plurality of inspection sets, and in the evaluating of the attention ability, the attention ability of the subject is evaluated based on the reaction time obtained in each of the plurality of inspection sets.

14. The attention ability inspection method according to claim 13, wherein a number of times of presentation of the central task is greater than a number of times of presentation of the peripheral task in the one inspection flow.

15. The attention ability inspection method according to claim 13, wherein in the randomly presenting of said at least one of the central task or the peripheral task, a timing from start of the inspection set to the presentation of the central task or the peripheral task is randomly changed.

16. The attention ability inspection method according to claim 13, wherein
a ratio of a number of times of presentation of the central task to a number of times of presentation of the peripheral task in the one inspection flow is changed.

17. The attention ability inspection method according to claim 9,
wherein the predetermined operation includes
a first operation corresponding to the central task, and
a second operation corresponding to the peripheral task and different from the first operation.

18. The attention ability inspection method according to claim 17, wherein
the peripheral graphic is a Landolt ring graphic, and
the second operation is an operation of indicating a direction in which the Landolt ring graphic is open.

19. The attention ability inspection method according to claim 9, further comprising:
in response to a relative positional relationship between the subject and the display area becoming a predetermined relationship,
setting a range of 3 degrees of vision of the subject as the central region in the display area, and
setting (i) a range surrounded by a boundary of an area of 60 degrees in a horizontal direction and 40 degrees in a vertical direction from a center of a line of sight of the subject, and (ii) a line obtained by offsetting the boundary inward by a predetermined distance, as the peripheral region in the display area.

20. The attention ability inspection method according to claim 9, wherein
the display area is divided into
(i) the central region,
(ii) the peripheral region located further outside than the central region, and
(iii) a middle region interposed between the central region and the peripheral region,
the central graphic is displayed only in the central region,
the peripheral graphic is displayed only in the peripheral region, and
neither the central graphic nor the peripheral graphic is displayed in the middle region.

* * * * *